United States Patent [19]

Shigematsu et al.

[11] 4,430,320

[45] Feb. 7, 1984

[54] RADIOACTIVE DIAGNOSTIC AGENT

[75] Inventors: Akiyo Shigematsu, Hachioji; Akira Tsuya, Tokyo; Michiaki Aihara; Akiko Suzuki, both of Kashiwa; Michiko Matsuda, Sakura, all of Japan

[73] Assignee: Kabushiki Kaisha Seitai Kagaku Kenkyusho, Tokyo, Japan

[21] Appl. No.: 309,764

[22] Filed: Oct. 8, 1981

[51] Int. Cl.³ ............... A61K 43/00; A61K 49/00
[52] U.S. Cl. .................. 424/1.1; 128/659; 562/602; 252/645
[58] Field of Search ............. 424/1, 1.5, 1.1; 252/301.1; 260/429.1; 128/1.1, 659; 562/602

[56] References Cited

U.S. PATENT DOCUMENTS

| | | | |
|---|---|---|---|
| 3,911,111 | 10/1975 | Swada et al. | 424/118 |
| 4,290,965 | 9/1981 | Stöcklin et al. | 260/408 |
| 4,308,249 | 12/1981 | Frank et al. | 424/1 |

OTHER PUBLICATIONS

Chemical Abstracts, vol. 95, (1981), p. 635, Abstract No. 203454k, Gilliland et al.

*Primary Examiner*—Benjamin R. Padgett
*Assistant Examiner*—M. Moskowitz
*Attorney, Agent, or Firm*—Birch, Stewart, Kolasch & Birch

[57] ABSTRACT

A radioactive diagnostic agent for renal cortex, adrenal cortex, myocardium, brain stem, spinal nerve, etc., which comprises as an essential component monoiodoacetic acid wherein the iodine atom is radioactive.

7 Claims, No Drawings

RADIOACTIVE DIAGNOSTIC AGENT

The present invention relates to a radioactive diagnostic agent. More particularly, it relates to a radioactive diagnostic agent comprising radioactive monoiodoacetic acid.

In recent years, the application of radioactively labeled compounds to the medical field, particularly nuclear medical diagnosis, has been rapidly developed. While acetic acid is known to play an important role in the metabolism of mammalian animals and human beings, it has now been found that the behavior of monoiodoacetic acid in those living bodies is quite similar to that of acetic acid, particularly in the organs and tissues including renal cortex, adrenal cortex, myocardium, brain stem, spinal nerve, etc. On the basis of such finding, this invention provides a radioactive diagnostic agent comprising as an essential component radioactive monoiodoacetic acid, i.e. acetic acid of which one hydrogen atom at the α-position to the carboxyl group is replaced by a radioactive iodine atom (e.g. $^{123}I$, $^{131}I$, $^{125}I$, $^{122}I$ ($\beta+$)), which is useful for nuclear medical diagnosis, particularly for imaging and dynamic study of renal cortex, adrenal cortex, myocardium, brain stem, spinal nerve, etc.

The radioactive diagnostic agent of this invention is characteristic in comprising monoiodoacetic acid wherein the iodine atom is radioactive.

The radioactive monoiodoacetic acid may be produced, for instance, by mixing non-radioactive monochloroacetic acid with radioactive sodium iodide in a suitable liquid medium. One of typical procedures comprises dissolving carrier-free $^{131}I$-sodium iodide (10 mCi) in acetone (20 ml), adding monochloroacetic acid (0.845 g) thereto and stirring the resultant mixture for 20 minutes, whereby the chlorine atom in the monochloroacetic acid is replaced by $^{131}I$ atom to give $^{131}I$-monoiodoacetic acid having a radioactivity of 5 mCi/1500 mg.

In addition to the radioactive monoiodoacetic acid as the essential component, the radioactive diagnostic agent of the invention may comprise any additive(s) conventionally employed in the related art field. Examples of such additive(s) are a pH controlling agent such as an acid, a base or a buffering substance, a stabilizer such as ascorbic acid, an isotonizing agent such as sodium chloride, a preserving agent such as benzyl alcohol, etc.

For preparation of the radioactive diagnostic agent of the invention, there may be adopted a per se conventional procedure. For instance, the said essential and optional components may be mixed together in an aqueous medium.

The radioactive element in the radioactive diagnostic agent should have sufficient radioactivity and radioactivity concentration which can assure reliable diagnosis, although any particular limitation is not present. The amount of the radioactive diagnostic agent to be administered to a human adult may be normally from about 0.5 to 5.0 ml, which usually includes a radioactivity of 0.1 to 50 mCi.

For the diagnostic purpose, the radioactive diagnostic agent may be administered to living bodies through vein, lumbar vertebra, dorsal vertebra, cervical vertebra, etc, by injection. Oral administration is also possible. Observation on the behaviors (e.g. absorption, distribution, metabolism, excretion) of the labeling material in various organs and tissues can be made, for instance, by the use of a scintillation camera, a computed tomography or the like. Through such observation, the morphological and functional differentiation of abnormal organs and tissues from normal ones can be made, and rapid and precise diagnosis becomes possible.

Advantageously, the radioactive monoiodoacetic acid as the essential component does not produce any material toxicity at its usual dose for the diagnostic purpose.

The present invention will be illustrated more in detail by the following Experiments and Examples wherein % is by weight, unless otherwise defined.

EXPERIMENT I

A male rat of Wistar strain weighing 100 grams (5 weeks old) was anesthetized by administration of 0.5 ml of a physiological saline solution of ketalar (2-(o-chlorophenyl)-2-(methylamino)-cyclohexanone) (50 mg/ml), and 0.1 ml of a physiological saline solution of $^{14}C$-carboxyl-monoiodoacetic acid (10 μCi/0.1 ml) was administered to the rat through the tail vein. The radioactivity distributions of the labeling material in the body after 5, 10, 20, 30, 60 and 180 minutes were quite similar to those of $^{14}C$-carboxyl-acetic acid, although in pancreas, $^{14}C$-carboxyl-monoiodoacetic acid did not show any characteristic uptake, whereas $^{14}C$-carboxylacetic acid did. Thus, remarkable uptake was recognized in renal cortex, adrenal cortex and myocardium. Further, over the entire period of observation, the distribution behavior of $^{14}C$-carboxyl-monoiodoacetic acid was almost the same as that of $^{14}C$-carboxyl-acetic acid.

For the above observation, an autoradiography was used. At a designed time after the administration of the labeling material, the rat was anesthetized with ether, frozen with liquid nitrogen and sliced with a cryomicrotome. The sliced piece was lyophilized and closely contacted onto an X-ray film. After one month, the film was subjected to treatment for photographing. Observation was made by taking the extent of blackening as the radioactivity concentration of the labeling material in the organs and tissues.

EXPERIMENT II

To a male rabbit weighing 2 kilograms, 0.1 ml of a physiological saline solution of $^{131}I$-monoiodoacetic acid (100 μCi/0.1 ml) was administered through an ear vein, and the distribution of the labeling material was observed by the use of a scintillation camera. Prior to the above administration, 30 mg of sodium iodide was given to the rabbit orally with drinking water once a day for three consecutive days. The distribution of $^{131}I$-monoiodoacetic acid in the rabbit was quite similar to that of $^{14}C$-carboxylmonoiodoacetic acid in Experiment I. Thus, remarkable uptakes were observed in renal cortex, adrenal cortex and myocardium. The distribution and behavior of the labeling material in the organs and tissues were also quite similar between them.

EXPERIMENT III

A male rabbit weighing 2 kilograms was anesthetized with administration of 0.5 ml of a physiological saline solution of ketalar (50 mg/ml), and 0.1 ml of a physiological saline solution of $^{131}I$-monoiodoacetic acid (10 μCi/0.1 ml) was injected into the lumbar vertebra. Then, the rabbit was kept in such manner that its head portion was inclined downwards at an angle of 30° to the horizontal direction, and after 30 minutes, $^{131}I$- monoiodoacetic acid flowed into the subarachnoid space, whereby clear images of cerebral ectocinerea, hypothalamus and cerebeller ectocinerea were produced. After one hour, $^{131}$I-monoiodoacetic acid disappeared gradually from brain and spinal nerve. After waking from anestesia, any abnormality in nervous conduction was not observed.

EXAMPLE 1

$^{131}$I-Monoiodoacetic acid was dissolved in physiological saline solution to make a concentration of 1 mCi/ml. The resulting solution was filtered through a microfilter to eliminate bacteria and filled in a vial. After the addition of benzyl alcohol as a preserving agent thereto to make a 0.9% concentration, the air above the solution in the vial was replaced by nitrogen gas.

EXAMPLE 2

$^{123}$I-Monoiodoacetic acid was dissolved in physiological saline solution to make a concentration of 1 mCi/ml. The resulting solution was filtered through a microfilter to eliminate bacteria and filled in a vial. After the addition of benzyl alcohol as a preserving agent thereto to make a 0.9% concentration, the air above the solution in the vial was replaced by nitrogen gas.

What is claimed is:

1. Monoiodoacetic acid wherein the iodine atom is radioactive.

2. A radioactive diagnostic composition, comprising: an effective imaging amount of monoiodoacetic acid wherein the iodine atom is radioactive and a pharmaceutically acceptable carrier therefor.

3. The composition according to claim 2, wherein 0.5 to 5.0 ml of said composition has a radioactivity of 0.1 to 50 mCi.

4. The composition according to claim 2, wherein said pharmaceutically acceptable carrier is a liquid medium.

5. The composition according to claim 2, wherein said pharmaceutical acceptable carrier is a physiological saline solution.

6. A method for nuclear medical diagnosis in mammals which comprises administering to said mammal a non-toxic effective imaging amount of the composition of claim 2 and imaging said mammal.

7. The method according to claim 6, wherein said method comprises diagnosis of the renal cortex, adrenal cortex, myocardium, brain stem or spinal nerve.

* * * * *